US011753325B2

(12) United States Patent
Shimose (10) Patent No.: US 11,753,325 B2
(45) Date of Patent: Sep. 12, 2023

(54) SYSTEM AND METHOD FOR TREATING OIL SLUDGE

(71) Applicant: Shimose Microbes Laboratory Corporation, Tokyo (JP)

(72) Inventor: Shinichi Shimose, Tokyo (JP)

(73) Assignee: Shimose Microbes Laboratory Corporation, Tokyo (JP)

( * ) Notice: Subject to any disclaimer, the term of this patent is extended or adjusted under 35 U.S.C. 154(b) by 31 days.

(21) Appl. No.: 17/615,270

(22) PCT Filed: May 25, 2020

(86) PCT No.: PCT/JP2020/020496
§ 371 (c)(1),
(2) Date: Nov. 30, 2021

(87) PCT Pub. No.: WO2020/241551
PCT Pub. Date: Dec. 3, 2020

(65) Prior Publication Data
US 2022/0220019 A1    Jul. 14, 2022

(30) Foreign Application Priority Data

May 31, 2019   (JP) ................................. 2019-102774

(51) Int. Cl.
*C02F 11/02*        (2006.01)
*C02F 11/13*        (2019.01)
(Continued)

(52) U.S. Cl.
CPC .............. *C02F 11/13* (2019.01); *C02F 11/02* (2013.01); *C10G 1/006* (2013.01);
(Continued)

(58) Field of Classification Search
CPC .............. C02F 11/00–20; C10G 1/006; C10G 33/00–08
See application file for complete search history.

(56) References Cited

U.S. PATENT DOCUMENTS

2021/0163326 A1*  6/2021  Ren .................... B01D 17/0205

FOREIGN PATENT DOCUMENTS

JP      H09-060848 A    3/1997
JP       4153685 B2    9/2008
(Continued)

OTHER PUBLICATIONS

English machine translation of JP 4153685 (Year: 2008).*
English machine translation of JP 2012-229403 (Year: 2012).*
English machine translation of JP 2004-161586 (Year: 2004).*

*Primary Examiner* — Renee Robinson
(74) *Attorney, Agent, or Firm* — Locke Lord LLP; James E. Armstrong, IV; Nicholas J. DiCeglie, Jr.

(57) ABSTRACT

An oil sludge treatment system includes: a reduced-pressure fermentation dryer; a filtration apparatus; and a cleaner. The reduced-pressure fermentation dryer is configured to: store oil sludge in an airtight container; heat and stir the oil sludge under reduced pressure so that a temperature of the oil sludge is within a predetermined temperature range; decompose organic matter contained in the oil sludge using microorganisms while evaporating water; and obtain volume-reduced dried product. The filtration apparatus filters oil from the dried product. The cleaner cleans, by steam, the dried product from which the oil has been filtered.

6 Claims, 6 Drawing Sheets

(51) Int. Cl.
  *C10G 1/00* (2006.01)
  *C02F 103/36* (2006.01)
(52) U.S. Cl.
  CPC .... *C02F 2103/365* (2013.01); *C02F 2303/06* (2013.01); *C10G 2300/1033* (2013.01)

(56) References Cited

FOREIGN PATENT DOCUMENTS

| JP | 2009-007563 A | 1/2009 |
| JP | 2012-229403 A | 11/2012 |
| JP | 2013-075248 A | 4/2013 |
| JP | 2016-095068 A | 5/2016 |

\* cited by examiner

SYSTEM AND METHOD FOR TREATING OIL SLUDGE

TECHNICAL FIELD

The present invention relates to a system and a method for treating oil sludge.

BACKGROUND ART

Patent Document 1 discloses, for example, a method and a device for treating oil sludge in which oil and mineralized slag are obtained from oil sludge accumulated in an oilfield or the bottom of an oil tanker.

Patent Document 1 is to provide a method and a device for treating oil sludge, which easily obtains oil of good quality and mineralized and harmless slag from oil sludge by stirring water-added oil sludge in an electrolysis tank to accelerate liquefaction of the oil sludge while reducing separation burden of a separator. However, such method and device require a complicated and large-scale plant, and thus results in expensive installation costs.

PRIOR ART DOCUMENTS

Patent Documents

[Patent Document 1] JP H09-060848 A
[Patent Document 2] JP 4153685

SUMMARY OF THE INVENTION

Problem to be Solved by the Invention

The present invention was made in consideration of the above circumstances, an object of which is to obtain oil of good quality from oil sludge accumulated in an oilfield or a bottom of an oil tanker by a plant made by combining versatile apparatuses. Also, an object of the present invention is to improve the environment, especially to reduce air pollution, of the oilfield by returning residual matter (soil) generated by the present invention to the oilfield.

Means for Solving the Problem

The present invention provides an oil sludge treatment system that includes a reduced-pressure fermentation dryer configured to: store oil sludge in an airtight container; heat and stir the oil sludge under reduced pressure so that a temperature of the oil sludge is within a predetermined temperature range; decompose organic matter contained in the oil sludge using microorganisms while evaporating water; and obtain volume-reduced dried product. The oil sludge treatment system further includes: a filtration apparatus that filters oil from the dried product; and a cleaner that cleans, by steam, the dried product from which the oil has been filtered.

In the present invention, the reduced-pressure fermentation dryer removes water from the oil sludge, and the filtration apparatus filters oil from the obtained dried product, and furthermore the cleaner cleans such treated dried product. Therefore, it is possible to discharge residual matter in a harmless and clean state. Thus, by returning the residual matter to an original site, it is possible to improve the environment, especially to reduce air pollution, of the oilfield and the like.

In the present invention, the filtration apparatus preferably includes: a feeding hole provided in an upper part of a main body of the filtration apparatus; a discharge outlet provided in a front part of the main body, which has an opening smaller than an opening of the feeding hole; a large number of slits provided in a bottom part of the main body so as to penetrate the bottom part; a screw extruder rotatable in a direction from the feeding hole to the discharge outlet; and an oil collecting part that is provided under the bottom part of the main body so as to collect the oil and that includes an oil discharge port. With this configuration, the filtration apparatus can be compact in size, and furthermore can easily filter oil from the dried product.

In the present invention, the cleaner preferably includes: a plurality of steam discharge nozzles provided above a conveyor body that transports the dried product from which the oil has been filtered; a large number of slits provided in a bottom part of the conveyor body so as to penetrate the bottom part; and a waste liquid collecting part that is provided under the bottom part of the conveyor body so as to collect cleaning drainage and that includes a drainage port. With this configuration, the cleaner can be compact in size, and furthermore can easily clean the dried product from which the oil has been filtered.

In the present invention, it is preferable that the oil collected in the bottom part of the filtration apparatus is further fed into a fuel inlet of a boiler via an oil pipe connected to the oil discharge port. Also, it is preferable that steam generated in the boiler is supplied to a heating jacket of the reduced-pressure fermentation dryer and the steam discharge nozzles of the cleaner via respective steam pipes. With this configuration, since the filtered oil can be used as fuel for the boiler, it is possible to reduce costs for fuel to be used in the boiler.

Also in the present invention, it is preferable that the cleaning drainage collected in a lower part of the cleaner is fed into the reduced-pressure fermentation dryer via a waste liquid pipe connected to the drainage port of the waste liquid collecting part. With this configuration, the oil sludge can be treated by the cleaning drainage, thus there is no need to discharge the cleaning drainage of the cleaning liquid.

Furthermore, an oil sludge treatment method of the present invention includes: a reduced-pressure fermentation drying step of: storing oil sludge in an airtight container; heating and stirring the oil sludge under reduced pressure so that a temperature of the oil sludge is within a predetermined temperature range; decomposing organic matter contained in the oil sludge using microorganisms while evaporating water; and obtaining volume-reduced dried product; a filtration step of filtering oil from the dried product; and a cleaning step of cleaning, by steam, the dried product from which the oil has been filtered. By this oil sludge treatment method, it is possible to obtain the same effects as those obtained by the above-described oil sludge treatment system.

Effect of the Invention

With the oil sludge treatment system and the oil sludge treatment method of the present invention, it is possible to remove a large amount of water from oil sludge by the reduced-pressure fermentation dryer. Also, it is possible to filter, by the filtration apparatus, oil from dried product obtained by the reduced-pressure fermentation dryer. Furthermore, it is possible to clean, by steam from the cleaner, the dried product from which the oil has been removed. Since the cleaning drainage is re-fed into the reduced-pressure fermentation dryer, the drainage step of discharging the cleaning drainage is not required. Moreover, since clean residual matter are generated from the dried product, it is possible to improve the environment, especially to reduce air pollution, of the oilfield by returning the residual matter to the oilfield. The residual matter can also be used as clean construction material.

MEANS FOR CARRYING OUT THE INVENTION

Figure 1:
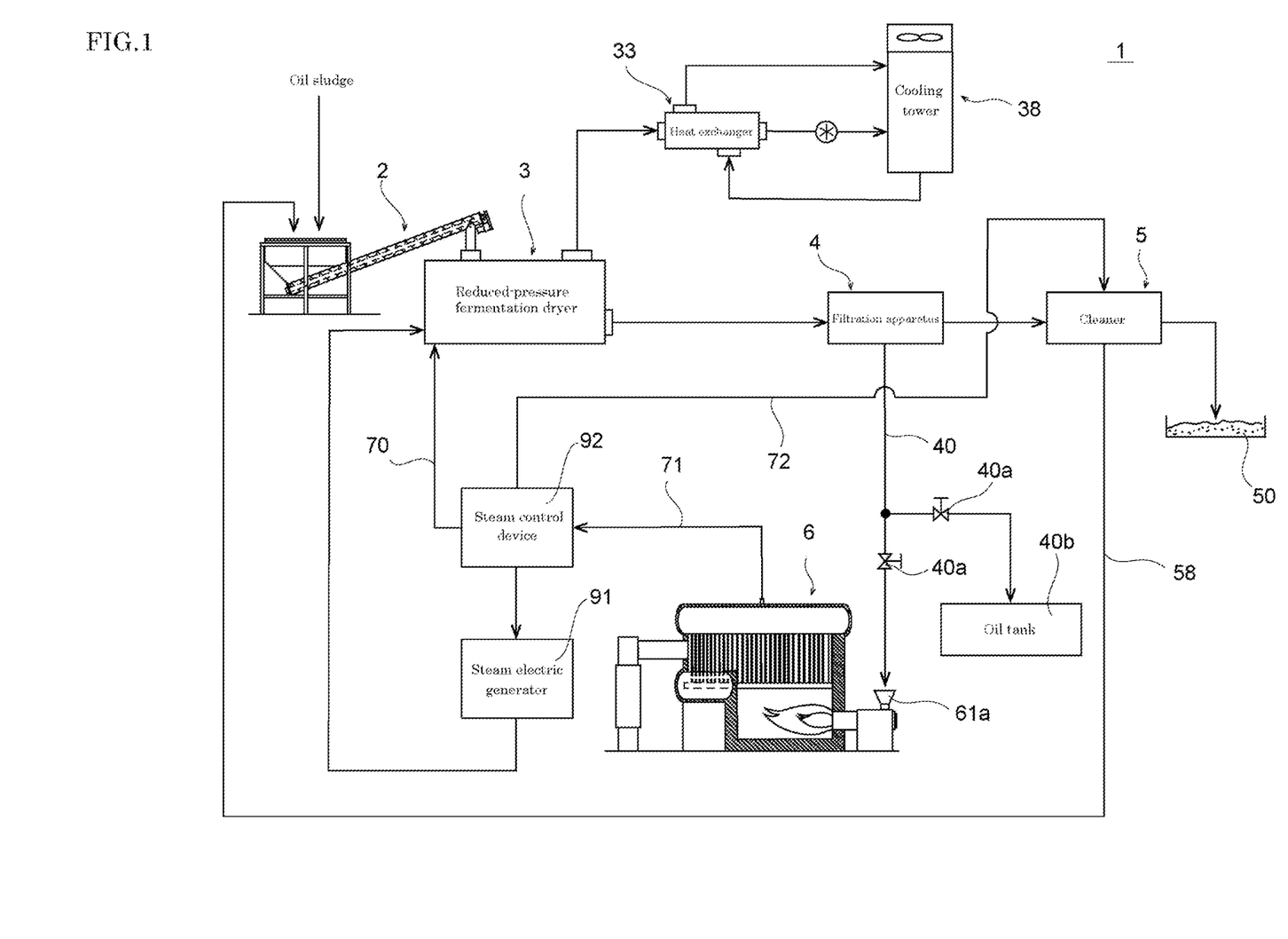
FIG. 1 is a block diagram illustrating a schematic configuration of an oil sludge treatment system according to an embodiment of the present invention.
Figure 2:
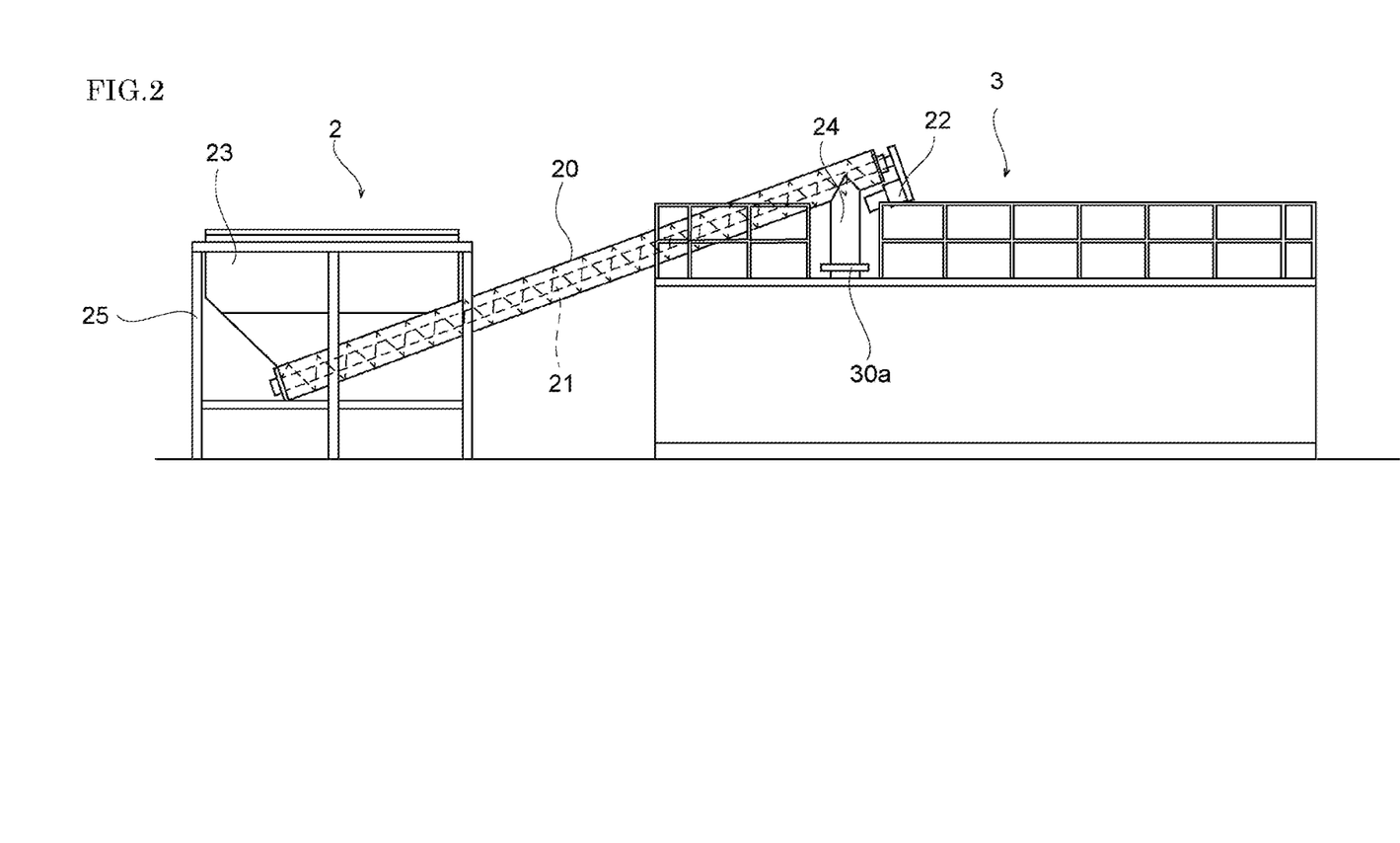
FIG. 2 is a front view illustrating a feeder and a reduced-pressure fermentation dryer in the oil sludge treatment system in FIG. 1.
Figure 3:
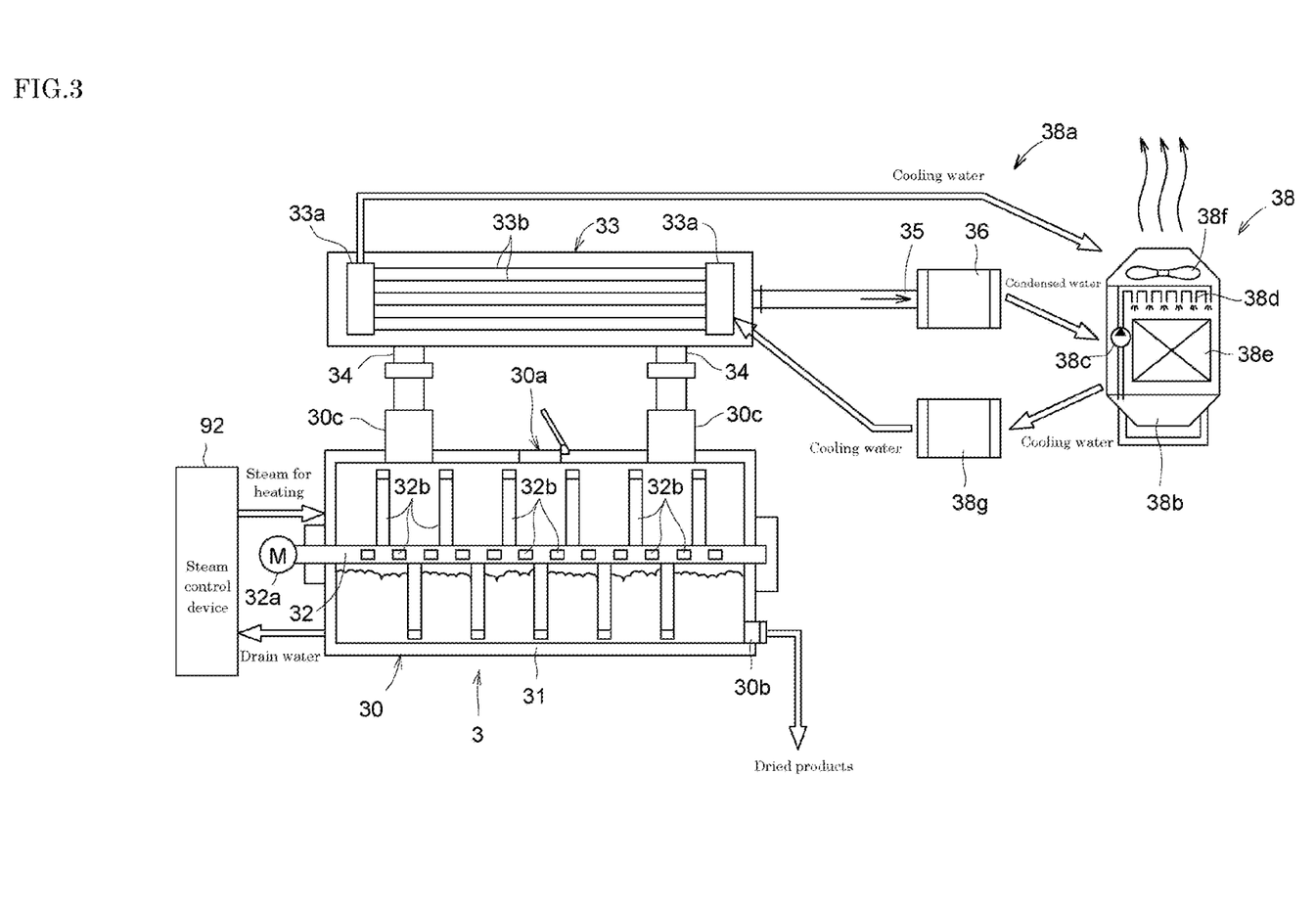
FIG. 3 is a diagram schematically illustrating a conceptual configuration of the reduced-pressure fermentation dryer provided in the oil sludge treatment system in FIG. 1.
Figure 4:
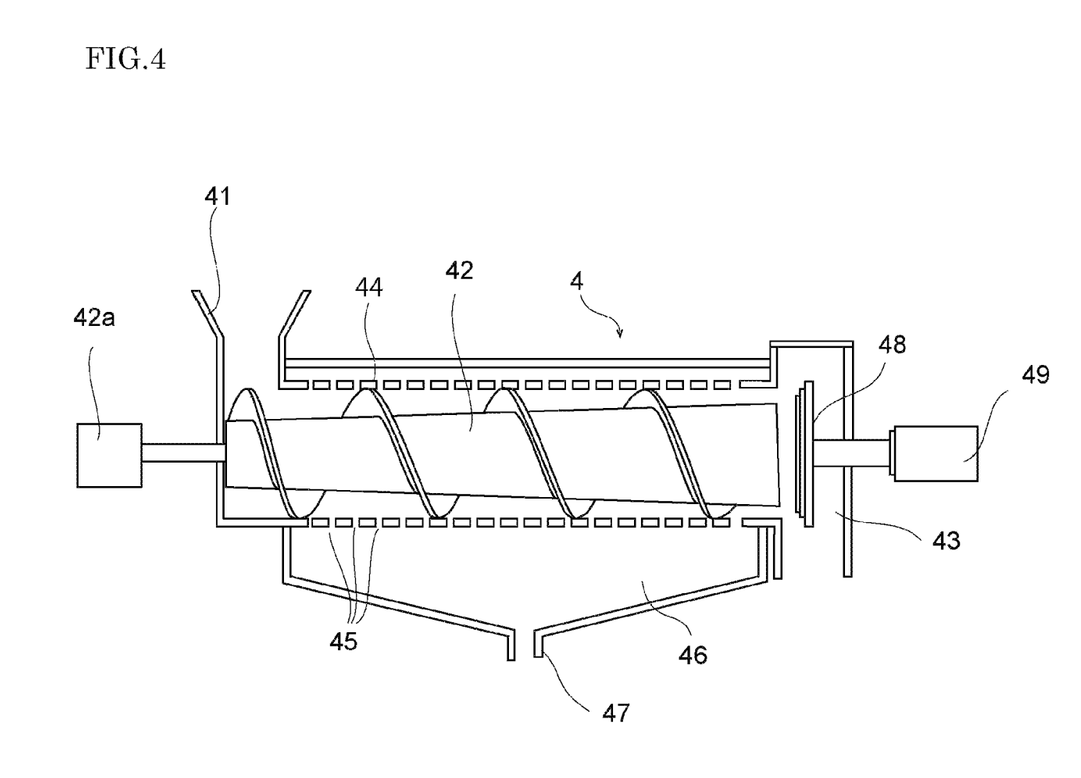
FIG. 4 is a cross-sectional view illustrating a schematic configuration of a filtration apparatus provided in the oil sludge treatment system in FIG. 1.
Figure 5:
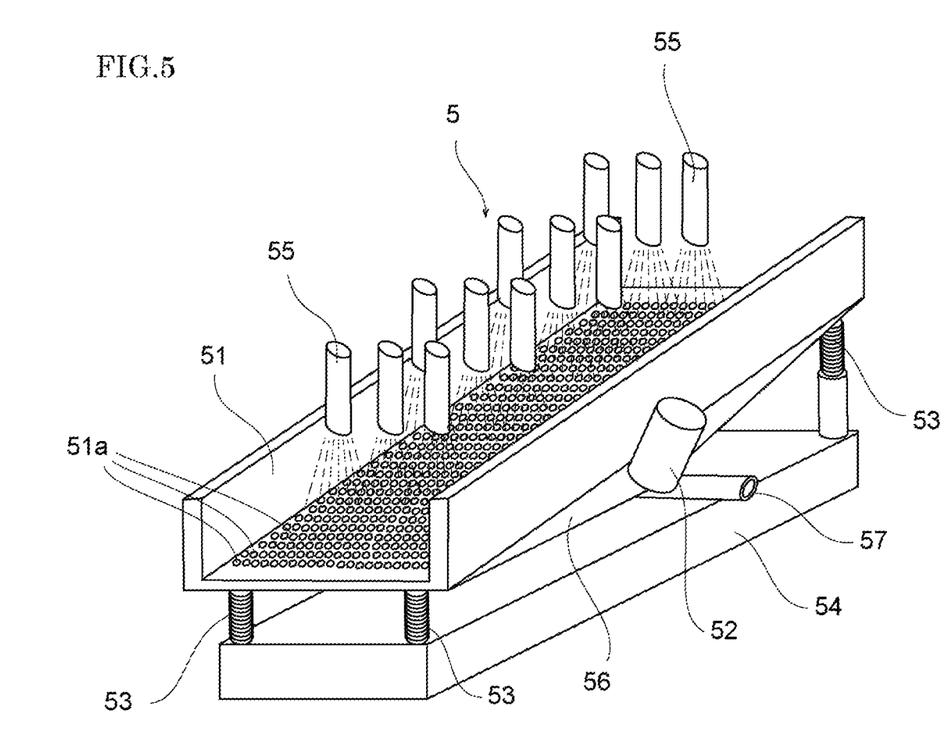
FIG. 5 is a perspective view illustrating a schematic configuration of a cleaner provided in the oil sludge treatment system in FIG. 1.
Figure 6:
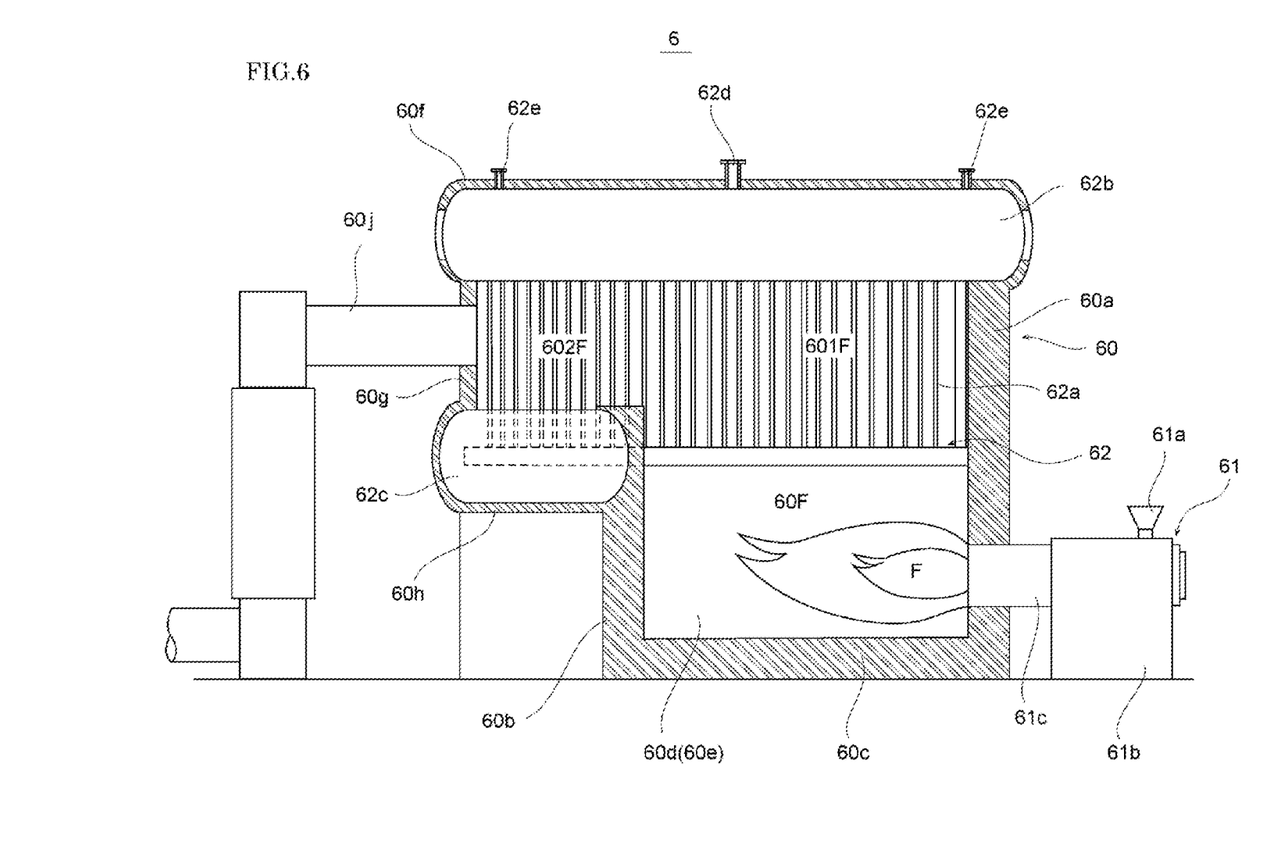
FIG. 6 is a cross-sectional view illustrating a schematic configuration of a boiler provided in the oil sludge treatment system in FIG. 1.

Hereinafter, an embodiment of the present invention will be described with respect to the drawings. FIG. 1 is a block diagram illustrating a schematic configuration of an oil sludge treatment system according to the embodiment of the present invention. FIG. 2 is a front view illustrating a feeder and a reduced-pressure fermentation dryer of oil sludge. FIG. 3 is a diagram schematically illustrating a conceptual configuration of the reduced-pressure fermentation dryer for fermenting and drying oil sludge under reduced pressure. FIG. 4 is a cross-sectional view illustrating a schematic configuration of a filtration apparatus for filtering dried product after the oil sludge is subjected to reduced-pressure fermentation drying. FIG. 5 is a perspective view illustrating a schematic configuration of a cleaner for cleaning the dried product. FIG. 6 is a cross-sectional view illustrating a schematic configuration of a boiler for supplying steam to the reduced-pressure fermentation dryer and the cleaner.

As shown in FIGS. 1 to 6, an oil sludge treatment system (hereinafter also simply referred to as the "treatment system") 1 includes: a feeder 2; a reduced-pressure fermentation dryer 3; a filtration apparatus 4; a cleaner 5; and a boiler 6. In the treatment system 1, for example, oil sludge accumulated in an oilfield or a bottom of an oil tanker is collected and stored in the feeder 2. The stored oil sludge is fed into the reduced-pressure fermentation dryer 3 by the feeder 2, and subjected to reduced-pressure fermentation drying in the reduced-pressure fermentation dryer 3. Dried product obtained by reduced-pressure fermentation drying in the reduced-pressure fermentation dryer 3 is transported to the filtration apparatus 4. Oil mixed with the dried product is removed by the filtration apparatus 4. The dried product from which the oil has been removed is transported to the cleaner 5 so that the dried product not containing the oil is cleaned by the cleaner 5. Thus, the dried product is discharged as clean residual matter. Since the residual matter does not contain impurities such as oil, it is possible to restore the environment to a state before extracting the oil by returning the residual matter to the original oilfield or the like. Thus, it is possible to sustain the natural environment.

Hereinafter, respective components included in the treatment system 1 are described in detail.

—Feeder—

The feeder 2 is to feed oil sludge stored in a hopper 23 (describer later) into a feeding hole 30a of the reduced-pressure fermentation dryer 3.

The feeder 2 includes: a cylinder body 20 of a transport conveyor that is inclined upward to the right in FIG. 2; a screw extruder 21 provided inside of the cylinder body 20; an electric motor 22 provided at the lower part of the distal end of the cylinder body 20; the hopper 23 provided on the upper part of the base end of the cylinder body 20 so as to store oil sludge; and a connecting section 24 provided in the lower part of the distal end of the cylinder body 20 so as to be connected to the feeding hole 30a of a tank 30 (described later). The hopper 23 is supported by a frame 25 so as not to fall down due to the weight of the oil sludge.

When the electric motor 22 is driven, the screw extruder 21 is rotated and thus the oil sludge on the bottom of the hopper 23 is stably fed into the tank 30 via the cylinder body 20 of the transport conveyor and the connecting section 24.

In addition, since the hopper 23 also stores cleaning drainage from the cleaner 5 (described later), the treatment system 1 is not required to have a waste water treatment device, and thus no harmful substances are discharged.

—Reduced-Pressure Fermentation Dryer—

The reduced-pressure fermentation dryer 3 is a publicly-known apparatus as described, for example, in Patent Document 2. The reduced-pressure fermentation dryer 3 is configured to: heat and stir organic waste as an object to be treated under reduced pressure so that the temperature of the organic waste is within a predetermined temperature range; decompose organic components of the organic waste using microorganisms while evaporating water; and obtain volume-reduced dried product.

More specifically, the water contained in oil of the oil sludge is trapped in the oil by organic components such as protein, and thus it does not evaporate easily. However, when the organic components are decomposed by microorganisms, the moisture is separated from the oil to be suspended moisture. Thus, by evaporating the suspended moisture, the volume-reduced dried product is obtained.

As schematically shown in FIG. 3, the reduced-pressure fermentation dryer 3 includes a substantially cylinder-shaped tank (pressure-resistant tank) 30 formed to have airtightness such that the pressure inside of the tank 30 is maintained equal to or lower than the atmospheric pressure. The tank 30 serves as an airtight container that stores the oil sludge supplied by the feeder 2. A heating jacket 31 is provided on a peripheral wall part of the tank 30. Steam for heating is supplied to the heating jacket 31 from the boiler. It is preferable that the temperature of the steam supplied from the boiler 6 is, for example, about 140° C.

In the tank 30, a stirring shaft 32 is disposed so as to extend in the longitudinal direction (left and right direction in FIG. 3) while it is surrounded by the heating jacket 31. The stirring shaft 32 is rotated by an electric motor 32a at a predetermined rotational speed. The stirring shaft 32 includes a plurality of stirring blades 32b that is separated from each other in the shaft direction. By the stirring blades 32b, the oil sludge is stirred, and then transported, after termination of the fermentation drying, toward the longitudinal direction of the tank 30.

The feeding hole 30a is provided in the middle of an upper part of the tank 30 in the longitudinal direction, which is for the oil sludge supplied from the feeder 2. The oil sludge that is fed through the feeding hole 30a is heated by the heating jacket 31 while stirred by the rotation of the stirring shaft 32. After elapse of a predetermined period of time, the dried product after treatment is discharged from a discharge section 30b provided in a lower part of the tank 30. In place of the electric motor 32a, a hydraulic motor may be used.

On the upper part of the tank 30, a guiding sections 30c, which guide steam generated from the heated oil sludge to a condensing section 33, are provided so as to protrude from the tank 30. In this embodiment, two guiding sections 30c are provided, and these two guiding sections 30c are disposed one by one on both sides of the tank 30 in the longitudinal direction with the feeding hole 30a being interposed therebetween. The condensing section 33 includes a plurality of cooling tubes 33b held by a pair of heads 33a. A cooling channel 38a is provided between the plurality of cooling tubes 33b and a cooling tower 38. In this embodiment, the condensing section 33 extends in the longitudinal direction of the tank 30 so as to be parallel with the tank 30. Also, the condensing section 33 is located behind the feeding hole 30a and the guiding sections 30c.

The temperature of the cooling water increases by heat exchange with the high temperature steam during flowing through the cooling tubes 33b of the condensing section 33. Then, as schematically indicated by the arrows in FIG. 3, the cooling water flows into a water receiving tank 38b of the cooling tower 38 via the cooling channel 38a. The cooling tower 38 is provided with: a drawing pump 38c that draws the cooling water from the water receiving tank 38b; and a nozzle 38d that sprays the drawn cooling water. The cooling water sprayed from the nozzle 83d flows downward through a downward flowing section 38e with being blown by a fan 38f, which lowers the temperature of the cooling water. Thus, the cooling water flows again into the water receiving tank 38b.

The cooling water cooled by the cooling tower 38 is transported by a cooling pump 38g and is sent to the condensing section 33 via the cooling channel 38a so as to pass through again the plurality of cooling tubes 33b. Then, after the temperature of the cooling water increases by heat exchange with the steam generated in the tank 30 as described above, the cooling water once again flows through the cooling channel 38a so as to flow into the water receiving tank 38b of the cooling tower 38. That is, the cooling water circulates through the cooling channel 38a between the condensing section 33 and the cooling tower 38. Also in this embodiment, the cooling water cooled by the cooling tower 38 is supplied to the condensing section 33 as described later. Thus, the cooling water circulates between the condensing section 33 and the cooling tower 38.

Apart from the circulating cooling water as described above, steam-condensed water also flows into the cooling tower 38, which is generated by the heated oil sludge and condensed in the condensing section 33. Although it is not shown in the drawings, the condensed water generated by heat exchange with the high temperature steam is accumulated in a lower part of the condensing section 33. Also, a vacuum pump 36 is connected to the condensing section 33 via a communication passage 35 so as to reduce the pressure in the tank 30.

Thus, when the vacuum pump 36 operates, air and condensed water are drawn from the condensing section 33 via the communication passage 35, and furthermore air and steam in the tank 30 are drawn via a communication passage 34 and the guiding section 30c. Accordingly, the condensed water is drawn from the condensing section 33 by the vacuum pump 36, and guided from the vacuum pump 36 to the water receiving tank 38b of the cooling tower 38 via a water conduit.

Thus, the condensed water introduced in the water receiving tank 38b of the cooling tower 38 is mixed with the cooling water. The mixed cooling water is drawn, as described above, by the drawing pump 38c so as to be sprayed by the nozzle 38d. After being sprayed, the cooling water flows downward through the downward flowing section 38e while being cooled. Since the condensed water contains the same microorganisms as those added to the oil sludge in the tank 30, an odor component or the like contained in the condensed water has been decomposed. Thus, the odor is not emitted outside.

—Operations of Reduced-Pressure Fermentation Dryer—

Here, operations of the above-configured reduced-pressure fermentation dryer 3 are described. The oil sludge stored in the tank 30 is heated by steam for heating supplied to the heating jacket 31 while being stirred by the rotation of the stirring shaft 32. The organic matter stored in the tank 30 is heated from the outside by the heating jacket 31 surrounding the inside of the tank 30 as well as heated from the inside by the stirring shaft 32 and the like. Thus, the temperature of the organic matter is effectively increased while the organic matter is stirred by the stirring shaft 32. Furthermore, since the pressure in the tank 30 is reduced due to operations of the vacuum pump 36, the boiling point is reduced in the tank 30 and thus the water evaporates at the temperature range in which decomposition of the organic components of the oil sludge is accelerated by the microorganisms.

It is preferable that the reduced-pressure fermentation drying step by the reduced-pressure fermentation dryer 3 takes, for example, 2 hours as one step (one cycle). First, the organic components of the organic matter are decomposed for 30 minutes in the fermentation step. When the inside of the tank 30 is decompressed to −0.06 to −0.07 MPa (gauge pressure, hereinafter this unit name is omitted), the water temperature inside of the tank 30 is maintained at 76 to 69° C. (saturated steam temperature). As a result, the fermentation and the decomposition of the organic matter is mainly promoted by the microorganisms described below.

Next, the fermenting organic matter is dried for 1.5 hours. For this purpose, the inside of the tank 30 is further decompressed to −0.09 to −0.10 MPa, thus the water temperature inside of the tank 30 is maintained at 46 to 42° C. (saturated steam temperature). As a result, the drying of the oil sludge is sufficiently promoted in the drying step. As to the microorganisms added to the oil sludge in the tank 30 at the time of drying treatment, it is preferable to use complex effective microorganisms, which are cultured in advance using a plurality of kinds of native microorganisms as a base, as described in Patent Document 2. That is, groups of so-called SHIMOSE 1, SHIMOSE 2 and SHIMOSE 3 have the majority of the colony.

Here, SHIMOSE 1 has the accession number FERM BP-7504 (internationally deposited with the Patent Microorganisms Depository of the National Institute of Advanced Industrial Science and Technology and the National Institute of Bioscience and Human-Technology of the Ministry of Economy, Trade and Industry (1-1-3 Higashi, Tsukuba, Ibaraki, Japan) on Mar. 14, 2003). Also, SHIMOSE 2 has the accession number FERM BP-7505 (internationally deposited in the same manner as SHIMOSE 1), which is microorganism belonging to the genus *Pichiafarinosa* having salt tolerance. SHIMOSE 3 has the accession number FERM BP-7506 (internationally deposited in the same manner as SHIMOSE 1), which is microorganism belonging to the genus *Staphylococcus*.

Here, the procedures of the reduced-pressure fermentation drying step of the organic matter by the reduced-pressure fermentation dryer 3 are described. First, the oil sludge containing organic matter is fed into the reduced-pressure fermentation dryer 3. At this time, the lid of the feeding hole 30a of the tank 30 of the reduced-pressure fermentation dryer 3 is opened to feed the oil sludge stored in the hopper 23 through the feeding hole 30a by feeder 2. Then, the lid of the feeding hole 30a is closed so that the inside of the tank 30 is kept at the atmospheric pressure.

Next, after adding the prescribed microorganisms to the oil sludge in the tank 30, the tank 30 is sealed by closing an atmosphere opening valve. Then, the inside of the tank 30 is heated under reduced pressure so as to promote fermentation and drying of the organic components of the oil sludge in the tank 30. Specifically, the inside of the tank 30 is heated by steam for heating that is supplied from the boiler 6.

The inside of the tank 30 is thus heated by the steam for heating while the stirring shaft 32 is rotated at a predetermined rotational speed (for example, about 8 rpm). Furthermore, the pressure in the tank 30 is reduced by operating the vacuum pump 36. Thus, the temperature inside of the tank 30 is optimized for microbial activity. As a result, decomposition of the organic components contained in the oil sludge is effectively promoted by the microorganisms. Here, the rotational speed (8 rpm) of the stirring shaft 32 is shown as an example, and any other rotational speed may be adopted to the extent that the organic components of the oil sludge can be decomposed.

When a predetermined period of time (for example, about 2 hours) is elapsed in the state in which the temperature and the pressure in the tank 30 are maintained, the operations of the vacuum pump 36 and the boiler 6 are stopped so that the pressure inside of the tank 30 becomes the atmospheric pressure. Furthermore, the stirring shaft 32 is reversely rotated and the lid of the discharge section 30b of the tank 30 is opened so as to discharge the dried product from the tank 30. At this time, the volume of the dried product that is discharged from the tank 30 has been reduced.

—Filtration Apparatus—

The dried product discharged from the discharge port 30b of the reduced-pressure fermentation dryer 3 is fed into the filtration apparatus 4. As schematically shown in FIG. 4, the filtration apparatus 4 is configured such that the dried product fed from an inlet nozzle 41 is transported to an outlet chute 43 by a worm screw 42 rotated by, for example, an electric motor 42a. In the process of the transport of the dried product, the gap between the worm screw 42 and a cylinder-shaped wall part 44 becomes gradually narrower. Thus, as the dried product is conveyed toward the outlet, the dried product is more filtered. Specifically, in the wall part 44 provided on the outer periphery side of the worm screw 42, a number of slits (openings) 45 are formed in a penetrating manner such that oil is filtered by the slits 45. The oil filtered by the slits 45 is collected in a collecting part 46, and after that, it is discharged from a discharge port 47 to the outside. The dried product transported to the end part of the worm screw 42 is also compressed by being sandwiched between the worm screw 42 and an outlet side plate 48. By adjusting the position of the outlet side plate 48 by a hydraulic cylinder 49, the dried product with a predetermined deoiling rate is discharged from the outlet chute 43.

In this way, the dried product from which the oil has been removed by the filtration apparatus 4 is sent from the outlet chute 43 to the cleaner 5. Also, the oil filtered by the filtration apparatus 4 is transported to a fuel inlet 61a of the boiler 6 via an oil pipe 40. Thus, the boiler 6 is combusted using the oil to generate steam. The generated steam is supplied to the heating jacket 31 of the reduced-pressure fermentation dryer 3 via a steam pipe 71, a steam control device 92 and a steam pipe 70. Accordingly, the tank 30 can be heated to ferment and dry the organic components of the oil sludge at an appropriate temperature.

In addition to the above, the surplus oil in the boiler 6 is stored in an oil tank 40b by appropriately opening and closing a valve 40a disposed in the middle of the oil pipe 40. Moreover, the oil stored in the tank 40b can be sold, and the money obtained by selling the oil can be used as working capital to drive the system.

—Cleaner—

The cleaner 5 is to remove impurities contained in the dried product transported from the filtration apparatus 4 by steam cleaning and thus to obtain clean residual matter 50 (soil). By returning this residual matter to the oilfield, the environment of the oilfield can be restored to its original state.

The cleaner 5 includes: a conveyor body 51, in a bottom surface of which are provided a number of slits (having the size of 1 to 5 mm) 51a in a penetrating manner; and a vibration motor 52 that vibrates the conveyor body 51. Also, the cleaner 5 is supported by a lower base 54 via a plurality of (for example, four) coil springs 53. The conveyor body 51 is provided in a state being inclined diagonally downward, and an upper side thereof is opened. Above the conveyor body 51, a plurality of steam discharge nozzles 55 is provided.

The steam discharge nozzles 55 are connected to the steam control device 92 via a steam pipe 72. Thus, the steam generated in the boiler 6 is sent to the steam discharge nozzles 55 in a state in which its discharge pressure is appropriately controlled by the steam control device 92.

In this way, the cleaner 5 is supported by the coil springs 53 in a floating state with respect to the lower base 54. Thus, the dried product in the conveyor body 51 is vibrated and transported forward by vibration of the conveyor body 51 caused by driving the vibration motor 52. On the way of the transport, the steam is sprayed to the dried product from the steam discharge nozzles 55 provided above. Thus, impurities contained in the dried product are filtered together with water droplets by the various number of slits 51a to be collected in a waste liquid collecting part 56 provided in the lower part of the conveyor body 51. From a drainage port 57 of the waste liquid collecting part 56, cleaning drainage flows through a waste liquid pipe 58 to be stored in the hopper 23 of the feeder 2. Therefore, in the cleaning step, the oil sludge can be treated without discharging drainage containing pollutants.

Also, it is possible to treat oil sludge accumulated in the bottom of an oil tanker in the same manner as described above. Thus, the oil sludge can be removed from the bottom of the oil tanker, and furthermore oil can be generated from the oil sludge without discharging drainage containing pollutants.

—Boiler 6—

The boiler 6 includes: a combustion furnace 60; a burner 61 disposed on the right side of the combustion furnace 60 in FIG. 6; and a heat exchanger 62 disposed in the combustion furnace 60.

First, the configuration of the combustion furnace 60 is described. The combustion furnace 60 includes three thick walls (a front wall 60a, a back wall 60b and a bottom wall 60c). A large-volume internal space of the combustion furnace 60 is constituted of these three walls, left and right side walls 60d and 60e, and a roof wall 60f. Thus, the internal space has a rectangle shape viewed from the side. The height of the back wall 60b is about a half the height of the front wall 60a. Behind the back wall 60b (on the left side in FIG. 6), a second back wall 60g is disposed. The second back wall 60g extends to the same height of the upper end of the front wall 60a. The lower end of the second back wall 60g is connected to the upper end of the back wall 60b via a second bottom wall 60h. Thus, a small-volume internal space is formed above the second bottom wall 60h. The small-volume internal space and the large-volume internal space constitute a combustion chamber 60F in the combustion furnace 60. For the sake of explanation, in the combustion chamber 60F, the internal space above the bottom wall 60c is hereinafter referred to as a "first combustion chamber 601F" while the internal space above the second bottom wall 60h is hereinafter referred to as a "second combustion chamber 602F". The walls 60a to 60h are made of, for example, refractory bricks or insulating material resisting a high temperature of approximately 1000° C.

Next, the configuration of the burner 61 is described. The burner 61 combusts fuel that is the oil obtained by filtering, using the filtration apparatus 4, the volume-reduced dried product treated by the fermentation dryer 3.

The burner 61 includes: the fuel inlet 61a; a combustor body 61b that generates mixed gas from the oil and a large amount of air supplied from an air supply port (not shown); and a combustor pipe 61c that combusts the mixture. The burner 61 generates swirling flame F in the first combustion chamber 601F, and combustion is consecutively continued in the second combustion chamber 602F. Thus, exhaust gas is generated and discharged to a discharge path 60j.

The heat exchanger 62 provided in the boiler 6 heats the water using combustion energy generated by the combustion of the fuel in the first combustion chamber 601F and the second combustion chamber 602F so as to generate hot temperature steam. The steam for heating generated by the heat exchanger 62 is supplied to the steam control device 92 via the steam pipe 71, and furthermore supplied from this steam control device 92 to the reduced-pressure fermentation dryer 3 (e.g. the heating jacket 31 of the tank 30).

More specifically, the heat exchanger 62 includes: a number of water tubes 62a; a steam-water drum 62b; and a water drum 62c.

The water flows through the various number of water tubes 62a, and evaporates by receiving the combustion energy of the fuel in the first combustion chamber 601F and the second combustion chamber 602F.

The steam-water drum 62b is a drum having a circular cross-section into which steam flows. The steam is generated by evaporation of the water that passes through the plurality of water tubes 62a. The steam-water drum 62b is located at a center position between the left side wall 60d and the right side wall 60e, and furthermore disposed so as to cover the first combustion chamber 601F and the second combustion chamber 602F. As shown in FIG. 6, the lower half of the steam-water drum 62b is located in the first combustion chamber 601F and the second combustion chamber 602F, and the upper half thereof is located above the roof wall 61f. A steam port 62c is opened in the middle part of the steam-water drum 62b in the front and back direction. The steam accumulated in the steam-water drum 62b is supplied from the steam port 62d to the steam control device 92 via the steam pipe 71. Water inlets 62e are respectively formed on both front and bask sides of the steam port 62d. The water from the water inlets 62e is supplied to the water drum 62c via the steam-water drum 62b and the water tubes 62a.

The steam accumulated in the steam-water drum 62b of the boiler 6 is supplied from the steam port 62d to the steam control device 92 via the steam pipe 71. After that, the steam is supplied to a steam electric generator 91 so that the steam electric generator 91 generates electricity by the supplied steam.

The steam electric generator 91 is constituted, for example, of a steam turbine generator that generates electricity by the supplied steam. Part of the electric power obtained by the electric generation is supplied to the reduced-pressure fermentation dryer 3 so as to be used as drive power of the reduced-pressure fermentation dryer 3. Thus, the costs for driving the reduced-pressure fermentation dryer 3 can be reduced. Also, the remaining part of the generated electric power is supplied to an electric power company. Thus, the money obtained by selling the electric power can be used as working capital to drive the system.

The boiler 6 has a configuration burning the oil obtained by filtration by the filtration apparatus 4 in the oil sludge treatment system 1. However, the boiler 6 may be applied to a boiler for combusting another substance.

The foregoing embodiment is to be considered in all respects as illustrative and not limiting. The technical scope of the invention is indicated by the appended claims rather than by the foregoing embodiment, and all modifications and changes that come within the meaning and range of equivalency of the claims are intended to be embraced therein.

INDUSTRIAL APPLICABILITY

The present invention is suitably applied to a system and a method for treating oil sludge by the reduced-pressure fermentation dryer.

DESCRIPTION OF REFERENCE NUMERALS

1 Oil sludge treatment system
2 Feeder
3 Reduced-pressure fermentation dryer
4 Filtration apparatus
40 Oil pipe
41 Feeding hole
41 Screw extruder
42 Discharge outlet
43 Slit
46 Oil collecting part
5 Cleaner
51 Conveyor body
55 Steam discharge nozzle
56 Waste liquid collecting part
57 Waste liquid pipe
6 Boiler
60 Combustion furnace
61 Burner
62 Heat exchanger

The invention claimed is:

1. An oil sludge treatment system comprising a reduced-pressure fermentation dryer configured to: store oil sludge in an airtight container; heat and stir the oil sludge under reduced pressure so that a temperature of the oil sludge is within a predetermined temperature range; decompose organic matter contained in the oil sludge using microorganisms while evaporating water; and obtain volume-reduced dried product, wherein the oil sludge treatment system further includes:
a filtration apparatus that filters oil from the dried product; and
a cleaner that cleans, by steam, the dried product from which the oil has been filtered.

2. The oil sludge treatment system according to claim 1, wherein
the filtration apparatus includes:
a feeding hole provided in an upper part of a main body of the filtration apparatus;
a discharge outlet provided in a front part of the main body, the discharge outlet having an opening smaller than an opening of the feeding hole;
a plurality of slits provided in a bottom part of the main body so as to penetrate the bottom part;
a screw extruder rotatable in a direction from the feeding hole to the discharge outlet; and
an oil collecting part provided under the bottom part of the main body so as to collect the oil, the oil collecting part including an oil discharge port.

3. The oil sludge treatment system according to claim 2, wherein
the oil that is collected in the oil collecting part of the filtration apparatus is further fed into a fuel inlet of a boiler via an oil pipe connected to the oil discharge port, and
steam that is generated in the boiler is supplied to a heating jacket of the reduced-pressure fermentation dryer and steam discharge nozzles of the cleaner via respective pipes.

4. The oil sludge treatment system according to claim 1, wherein
the cleaner includes: a plurality of steam discharge nozzles provided above a conveyor body that transports the dried product;
a plurality of slits provided in a bottom part of the conveyor body so as to penetrate the bottom part; and
a waste liquid collecting part provided under the bottom part of the conveyor body so as to collect cleaning drainage, the waste liquid collecting part including a drainage port.

5. The oil sludge treatment system according to claim 4, wherein
the cleaning drainage collected in the waste liquid collecting part of the cleaner is fed into the reduced-pressure fermentation dryer via a waste liquid pipe connected to the drainage port of the waste liquid collecting part.

6. An oil sludge treatment method comprising:
a reduced-pressure fermentation drying step of: storing oil sludge in an airtight container; heating and stirring the oil sludge under reduced pressure so that a temperature of the oil sludge is within a predetermined temperature range; decomposing organic matter contained in the oil sludge using microorganisms while evaporating water; and obtaining volume-reduced dried product;
a filtration step of filtering oil from the dried product; and
a cleaning step of cleaning, by steam, the dried product from which the oil has been filtered.

* * * * *